United States Patent [19]

Owen et al.

[11] Patent Number: 5,866,099

[45] Date of Patent: Feb. 2, 1999

[54] MAGNETIC-POLYMER PARTICLES

[75] Inventors: Charles S. Owen, Swarthmore, Pa.; John C. Silvia, Lindenwold; Louis D'Angelo, Berlin, both of N.J.; Paul A. Liberti, Churchville, Pa.

[73] Assignee: Nycomed Imaging AS, Oslo, Norway

[21] Appl. No.: 846,575

[22] Filed: Apr. 30, 1997

Related U.S. Application Data

[63] Continuation of Ser. No. 231,323, Apr. 22, 1994, which is a continuation of Ser. No. 971,513, Nov. 3, 1992, abandoned, which is a continuation of Ser. No. 245,351, Sep. 16, 1988, abandoned, which is a continuation of Ser. No. 906,521, Sep. 16, 1986, Pat. No. 4,795,698, which is a continuation-in-part of Ser. No. 784,863, Oct. 4, 1985, abandoned.

[51] Int. Cl.$^6$ .................................................. A61B 5/055
[52] U.S. Cl. ..................... 424/9.322; 424/9.323; 424/646; 424/648
[58] Field of Search ............................. 424/9.322, 9.323, 424/646, 648; 436/173; 428/551; 514/6, 54, 57, 59; 600/420

[56] References Cited

U.S. PATENT DOCUMENTS

| | | | |
|---|---|---|---|
| 4,157,323 | 6/1979 | Yen et al. | 260/29.7 M |
| 4,452,773 | 6/1984 | Molday | 424/1.1 |
| 4,501,726 | 2/1985 | Schröder | 424/1.1 |
| 4,615,879 | 10/1986 | Runge et al. | 424/9 |
| 4,675,173 | 6/1987 | Widder | 424/9 |
| 4,719,098 | 1/1988 | Weinmann et al. | 424/9 |
| 4,731,239 | 3/1988 | Gordon | 424/9 |
| 4,744,760 | 5/1988 | Molday | 435/7.2 |
| 4,770,183 | 9/1988 | Groman et al. | 424/9.32 |
| 4,795,698 | 1/1989 | Owen et al. | 435/4 |
| 4,849,210 | 7/1989 | Widder | 424/9.322 |
| 4,986,980 | 1/1991 | Jacobsen | 424/9.35 |
| 5,746,999 | 5/1998 | Gries et al. | 424/9.322 |

*Primary Examiner*—Gary E. Hollinden
*Attorney, Agent, or Firm*—Lyon & Lyon LLP

[57] ABSTRACT

A magnetic-polymer particle, useful in immunoassay techniques and various other biological/medical applications is produced by coprecipitation of transition metals in the presence of a polymer having available coordination sites. These particles are capable of forming stable aqueous suspensions and may be easily resuspended after agglomeration.

1 Claim, No Drawings

MAGNETIC-POLYMER PARTICLES

This is a continuation of a co-pending application Ser. No. 08/231,323, filed Apr. 22, 1994, which is a continuation of U.S. Ser. No. 07/971,513, filed Nov. 3, 1992 now abandoned, which is a continuation of U.S. Ser. No. 07/245,351, filed Sep. 16, 1988 now abandoned, which is a continuation of U.S. Ser. No. 06/906,521, filed Sep. 16, 1986, now U.S. Pat. No. 4,795,698, which is a continuation-in-part of U.S. Ser. No. 06/784,863, filed Oct. 4, 1985 now abandoned. All of the above-identified patents and applications are expressly incorporated by reference.

BACKGROUND OF THE INVENTION

This invention pertains to particles comprised of certain polymers in combination with magnetic metals, to compositions including such particles, and to methods of making and using such particles and compositions. More particularly, this invention pertains to such particles in which the polymer has a biochemical function.

Biologically active magnetic particles may find use in a variety of preparative and diagnostic techniques. Among these is high gradient magnetic separation (HGMS) which uses a magnetic field to separate magnetic particles from suspension. In instances where these particles are attached to biological materials of interest (e.g. cells, drugs), the material of interest may thereby be separated from other materials not bound to magnetic particles.

Several properties are important if a magnetic particles is to be useful in biological and diagnostic systems. First, the particle must possess the necessary biological activity, affinity, or reactive nature, by which it will perform its function. Second, the particles must be suspendable in an aqueous medium for delivery to the biological or reaction system. It may also be desirable that the particle suspension be stable (i.e. not settle out or agglomerate). Finally, small particle size may be desirable to that a suspension of the magnetic particles may be filter sterilized by conventional techniques.

Many techniques have been suggested in the prior art for the preparation of magnetic particles or organomagnetic materials. U.S. Pat. No. 4,001,288 to Gable et al. discloses a preparation of magnetic organo-iron compounds which are both water soluble and strongly magnetic. In the preparation taught by Gable et al., ferrous iron in solution is treated with hydrogen peroxide and then with ammonium hydroxide in order to precipitate an iron oxide compound. This compound is subsequently oxidized with peroxide, treated with a hydroxy-carboxylic acid, and reacted with an alkaline material in order to form a soluble product.

Gable et al., also disclose the introduction of proteins or "protein degradation products" into the ferrous iron solution which is subsequently reacted to precipitate iron oxides. The only material for which examples are presented is the hydrolysis product of gelatin treated with hydrogen peroxide.

U.S. Pat. No. 4,452,773 to Molday discloses "colloidal sized" iron oxide particles coated with a polysaccharide, (exemplified in the patent by dextran and dextran derivatives). Although Molday's particles are prepared in a manner somewhat similar to that used in preparing particles in the present invention, they are believed to be substantially different from the particles of the present invention.

U.S. Pat. No. 4,454,234 to Czerlinski teaches the preparation (generally by suspension polymerization on a magnetic particle substrate) of coated magnetic particles which are reversibly suspendable in solution. The suspension parameters taught by Czerlinski involve the effect of the Curie temperature of his magnetic particles which may be used alternately to cause the particles to be magnetic and non-magnetic. When the particles are magnetic, they tend to agglomerate, but may be resuspended after heating the particles to a temperature above the Curie temperature of the magnetite contained therein.

U.S. Pat. No. 4,230,685 to Senyei, et al., discloses the preparation of microspheres containing magnetite, albumin, and protein A. The preparation taught by Senyei does not involve the precipitation of magnetite in the presence of these other constituents, but rather is a coating of performed magnetite particles.

Other patents which may be considered to be of interest include U.S. Pat. No. 4,152,210 to Robinson, et al.; U.S. Pat. No. 4,335,094 to Mosbach; U.S. Pat. No. 4,018,886 to Giaever; and U.S. Pat. No. 4,070,246 to Kennedy, et al. While these patents all disclose the preparation or use of magnetic-biologic particles, none of these are thought to be similar to those of the present invention.

Glossary

Active Halogen: A halogen atom bonded to a carbon atom which is either bonded to or adjacent to a carbon bonded to an electron-withdrawing group. (For example: iodo-acetamide, iodo-acetate)

Available coordination Site: A coordination site which is not sterically hindered (can be freely approached) and is adapted to coordinate a metal atom in metal compounds (e.g. $Fe_3O_4$).

Biofunctional Ligand: A molecule having biological activity or a particular affinity in a biological system which can be linked to the ferromagnetic-polymer particles of this invention so as to impart particular biological properties to those particles.

Coordination Sites: An atom in a molecular structure which has a "free" electron pair capable of forming a coordinate bond with a transition metal atom.

Denatured Proteins: Proteins which have lost a specific biofunctional activity (e.g. enzymatic, antigenic, antibody, etc.) through a chemical or structural alteration. As used by Gable et al: Protein residues remaining following cleavage of some amide bonds and having molecular weights <10,000.

Extra-Particulate Bonds: Linking of one functional group of a bifunctional compound to a site on a ferromagnetic-polymer particle while the other functional group is linked to a site on a different molecule or (typically a "ligand").

Ferromagnetic: Permanently magnetic iron compositions (having a net magnetic moment).

Intra-Particulate Bonds: Linking of both functional groups of a bifunctional compound to different sites on the same magnetic-polymer particle.

Low Ionic Strength: An aqueous solution of near-neutral pH and having a total concentration of cations (usually from a buffer) of <40 mM.

Protein: Amino acid polymers linked with amide (peptide) bonds and having molecular weights >10,000.

Resuspendable: A material which once agglomerated (e.g. by centrifugation, HGMS, or flocculation) is capable of being redispersed to yield a stable suspension.

Sonication: Exposure to high intensity ultrasound.

Stable Suspension: A suspension which does not settle or otherwise agglomerate if left quiescent at standard temperature and pressure for 2 days.

BRIEF DESCRIPTION OF THE INVENTION

The present invention comprises a process for the preparation of suspendable and resuspendable magnetic-polymer particles and the particles produced thereby. Such particles exhibit useful properties, particularly in immunoassays wherein the particles are prepared with a particular biofunctional ligand and are subsequently separated by high gradient magnetic separation techniques.

The process of the invention includes the coprecipitation of metal ions (e.g. [Fe(II)+Fe(III)] or [Fe(II)+Cr(III)]) as magnetic compounds in the presence of a polymer having available coordination sites, reaction of the polymer and the metal to form a precipitate and recovery of the magnetic-polymer particles. Additionally, various biofunctional groups may be incorporated into the particles in order to yield an effective biofunctional reagent for use in immunoassay, cell capture, enzyme immobilization reactors, NMR imaging, and other diagnostic and analytical techniques.

DETAILED DESCRIPTION OF THE INVENTION

According to one embodiment of the present invention, a solution containing Fe(II) and Fe(III) (typically $FeCl_2$ and $FeCl_3$), and a polymer (e.g. a protein) having available coordination sites is treated (by titration or otherwise) with a strong base such as ammonium hydroxide ($NH_4OH$) in order to precipitate magnetic iron oxides such as magnetite ($Fe_3O_4$) in a form which is intimately combined with the polymer. The precipitation is typically carried out with rapid stirring and optional agitation by sonication, in order to produce resuspendable magnetic-polymer particles.

After precipitation, the particles are washed and subsequently resuspended in a buffer solution at approximately neutral pH.

Other embodiments of the present invention involve the use of metals other than iron in the coprecipitation reaction. In particular, Fe (III) may be replaced by any of a wide range of transition metal ions. In some cases, iron may be completely supplanted by appropriately selected transition metal ions. In many cases, the sue of metals other than ion produces colored particles ranging from white to dark brown.

Magnetic-polymer particles prepared according to the present invention exhibit many useful properties. These particles are magnetic due to the inclusion of a form of magnetic metal compound (e.g. iron similar in form to magnetite, or a similar compound). The particles may be formulated to be resuspendable after aggregation and to produce relatively stable suspensions which do not settle even after several days of quiescent storage. Furthermore, particles produced according to the present invention may be relatively small (approximately 0.01–0.2 micron) and therefore filter sterilizable. Finally, particles produced according to the present invention can be tailor-made to include specific biofunctional ligands useful in various analytical, diagnostic, and other biological/medical applications.

Subsequent to precipitation and resuspension of the magnetic-polymer particles, they may be treated with a bifunctional reagent in order to cross-link reactive sites present on the polymer. This cross-linking may be effective as either an intro-particulate cross-linking in which reactive sites are bound on the same particle, or may be a reaction of an extra-particulate ligand which is then cross-linked to the polymer on a given particle. In the second case, a bifunctional reagent having a relatively short distance between its two functional groupings is desirable to promote linkage between the particle polymer and the extra-particulate species. Conversely, intro-particulate cross-linking is promoted by the use of a bifunctional reagent which is longer and is not sterically hindered from bending so that two reactive sites on a single particle may be linked by a single bifunctional molecule.

As an alternative to the use of sonication during either the precipitation or resuspension steps outlined above, another type of agitation (such as mechanical stirring) may be employed.

Resuspension of the magnetic-polymer particles of the invention is typically carried out in a low ionic strength buffer system (e.g. 40 mM phosphate). The buffer system enables resuspension of particles which are not resuspendable in non-ionic solution. In addition to phosphate buffers, borate and sulfate systems may also be used.

The intimate association of polymer and metal in the present invention is thought to result from coordination of metal present during coprecipitation by coordination sites on the polymer. It is hypothecated that certain coordination sites are more "available" than other, based on both the strength of the coordinate bond which may be formed by the particular atom, and the spatial hindrances imposed by surrounding atoms. It is known, for instance, that oxygen atoms having a "free" electron pair complex iron more strongly than amine nitrogen atoms and, to an even greater degree, a hydroxyl oxygen atom. Thus, a polymer bearing oxy-acid functional groups should provide better product particles than an amine-substituted polymer. Similarly, coordination sites which may be freely approached to close distances should yield better performance than sites which are hindered in either a path of approach or in approach distance.

The above-described trends are qualitatively observable in various experiments performed by the present inventors. The presence of "available coordination sites" appears necessary to the production of the resuspendable magnetic-polymer particles of the present invention. For example, such diverse polymers as natural proteins, synthetic proteins, poly-amino acids, carboxy-poly-alkyls, alkoxy-poly-alkyls, amino-poly-alkyls, hydroxy-poly-alkyls, and various copolymers of these have all been demonstrated to produce the particles of the present invention. In addition, other polymers such as sulfoxy-poly-alkyls, poly-acrylamines, poly-acrylic acid, and substituted poly-alkylenes produce the particles of the present invention.

In selecting the transition metals to be employed in the coprecipitation reaction, several criteria appear to be important. First, the final compound must have one or more unpaired electrons in its structure. Second, one of the metals must possess an available coordination site for bonding to a polymer. Third, the coprecipitate must be capable of forming a cubic close-packed or hexagonal close-packed (e.g. for cubic: spinel or inverse spinal) crystalline structure. This last requirement is thought to result from the need for a very close packing in order for a compound to be magnetic.

Finally, polymers useful in preparing the particles of the present invention may be "tailor-made" to include monomers which exhibit a specific biofunctional activity. Using such a polymer permits direct precipitation of a biofunctional magnetic-polymer particle which requires little or no further treatment in order to be useful in assays which rely on the particular biofunctional activity of the polymer.

In certain applications, larger, less stable particles are useful. The particles of the present invention may be made to agglomerate while still retaining both their biofunctional and magnetic characteristics. Agglomeration of the particles may be accomplished by treatment of a suspension with a predetermined amount of, for example, barium chloride solution. This treatment may be designed to cause the particles to settle out of suspension in a predetermined period of time in order to allow the performance of further procedures, or to allow the larger particles to be easily attracted by relatively small magnets.

The following examples serve to illustrate various parameters of magnetic-polymer particle preparation and use:

EXAMPLE 1

General Preparative Procedure

The starting aqueous solutions for a typical (micro) preparation are as follows:

1 mg./ml solution of a given protein
500 mg./ml $FeCl_3$
200 mg./ml $FeCl_2$
20 mM phosphate buffer (approximately pH 7)
7.5% or 15% ammonium hydroxide solution ($NH_4OH$)

The preparation begins by diluting 2.5 ml of the protein solution to a volume of 20 ml with distilled water. 175 ul of the $FeCl_2$ and 140 ul of the $FeCl_3$ is added. Finally, about 200 ul of ammonium hydroxide solution is added.

It should be noted that the amount of base added is usually pre-calculated to allow for the gross amount of protein or polymer in the reaction mixture and the buffering ability of that particular protein or polymer. The objective is to raise the pH to a sufficient degree to permit precipitation of the iron oxides, but to retain the essential activity of the protein or polymer by not exceeding the pH at which that material denatures.

These materials are all added to the reaction vessel with continuous agitation in order to promote a homogeneous reaction mixture. Immediately upon addition of the base ($NH_4OH$), black particles precipitate. The reaction mixture is centrifuged, typically at 3,000 rpm for 15 minutes and the supernatant is discarded. The pellet is then broken up and the material washed in 20 ml of phosphate buffer, typically for three wash cycles, with centrifugation. After the final wash, the pellet is again broken up and the material resuspended in buffer, under the influence of sonication. The final solution is a transparent amber or brown solution which is a stable suspension of ferromagnetic-polymer particles. Throughout the procedure, no residual aggregate of iron is ever observed.

Subsequent treatment of the particles may proceed by any of the procedures detailed below, including intro-particulate cross-linking, or extra-particulate cross-linking to biofunctional reagents.

EXAMPLE 1A

Use of Metals Other Than Iron

As described above, metals other than iron may be incorporated into the magnetic-polymer particles of the present invention. Presented below is a (non-exhaustive) table of those ions which may be used in preparation of magnetic-polymer particles:

Co(II)+Ga(III)
Ga(III)+Er(III)
Co(II)+Ru(III)
Ga(III)+Ru(III)
Co(II)+Mn(II)
Ga(III)+Mn(II)
Ga(III)+V(III)
Co(II)+V(III)
Ga(III)+Mo(V)
Ga(III)+Fe(III)
V(III)+Fe(III)
Mn(II)+Ru(III)
V(III)+Mn(II)
Co(II)+Mo(V)
Cr(III)+Ga(III)
Cr(III)+Mn(II)
Er(III)+Ru(III)
Er(III)+Co(II)
Mn(II)+Er(III)
Cr(III)+Fe(II)

In addition to the list above, Fe(II) may be used in combination with selected transition metal ions whose electromotive potential is insufficient to oxidize the Fe(II) to Fe(III). Of the above listed metals, only V(III) is capable of oxidizing the Fe(II), and is therefor unsuitable.

EXAMPLE 2

Particles Coupled to Antibodies

Two solutions (each 40 ml) were mixed rapidly in an ultrasonic bath to promote mixing. Both contained 1.5 mg/ml bovine serum albumin (BSA). One contained ammonium hydroxide (8 ml of 30%, final concentration=74 mM). The other contained 140 mg of Fe(II) Chloride and 280 mg of Fe(III) Chloride (total iron concentration, 1 mg/ml after mixing). A black precipitate immediately formed. The mixture was neutralized by addition of 6 ml of glacial acetic acid while stirring. The sample was divided into 4 tubes and the precipitate was washed by centrifugation (3000 rpm, 15 min) and the small amount of iron remaining in the gold-colored and slightly cloudy supernatent was discarded. The pellet was resuspended in 20 ml of 20 mM phosphate buffer at neutral pH. Each of the 4 tubes containing 5 ml of particles was sonicated for 5 min in a Branson Sonifier with a cup horn attachment.

The available amino groups on the particles were reacted with succinimidyl-propiono-dithiopyridine (SPDP) to prepare a portion of them for later coupling to antibody. This reaction (20 ml particles+5 mg SPDP) proceeded for 1 hour in the cold with stirring. Then 25 mg of the amino-reactive cross-linking reagent ethylene-glycol-disuccinimide-ester (EGS) was added to further stabilize the particles. The mixture was reacted for a further hour with stirring. The EGS cross-linked any remaining amino residues which were in close enough proximity to be coupled. Other remaining amino groups would have been bound by one of the ends of the EGS molecule while the other would eventually hydrolyze to a carboxylic group. This results in a net conversion of positively charged to negatively charged groups on the particle surface which is thought to promote stability of the colloidal suspension.

At the end of the reaction period, the preparation was transferred to a 50 ml tube and 10 ml of 3-molar NaCl solution in water was added to "salt out" the particles. After allowing 10 minutes at room temperature for aggregation, the particles were centrifuged at 1500 rpm for 10 minutes. The clear colorless supernatant was discarded. The pellet was resuspended and centrifuged two more times before receiving a final suspension in 20 ml of 20 mM phosphate buffer (no sonication was usually necessary at this point).

Particles were coupled to goat antiserum specific for horseradish peroxidase, as a conveniently assayed antigen. Antiserum was activated by reaction with SPDP. For 30 minutes at room temperature, 0.128 ml of antiserum, containing 1.28 mg total protein, was reacted with 12.8 micrograms of SPDP, diluted into 0.512 ml phosphate buffer. After 30 minutes 3.1 mg dithiothreitol (DTT) was added to convert the SPDP to its free sulfhydryl form. The reacted Ab was separated (desalted) on a small gel filtration column.

Thiolated antiserum and SPDP-activated particles were reacted by the addition of 6.4 ml containing the antibody (0.64 mg of antiserum protein if there was 100% recovery) to particles containing 14 mg of iron. Concentrations in the reaction mixture were 1.0 mg/ml for antiserum protein and 2.2 mg/ml for particle iron, in a total volume of 6.4 ml. After an hour at 4° C., the particles were salted out and washed. The pellet was resuspended in 3.2 ml phosphate buffer, with sonication, for 1 minute.

The antigen-binding activity of the magnetite-bound antiperoxidase was assayed by incubating an aliquot of particles with free horseradish peroxidase (HRP), salting out the particles, washing them and assaying the resuspended particles for enzyme activity in a colorogenic assay. The antibody-coupled particles took up more than ten times as much enzyme as a control particle preparation which was coupled to a similar antibody that was specific for an irrelevant antigen.

EXAMPLE 3

Particles Containing a Radioiostope of Iodine

Particles were formed by the method described in Example 2, with the exceptions that a small amount of radio-iodinated ($^{125}$I) BSA was added to the reaction as a tracer for the protein component, and that four preparations were made which varied the amounts of iron and BSA in the precipitation reaction as follows:

A. 1.25 mg Fe/ml and 1.5 mg BSA/ml (usual concentrations)
B. 3.75 mg Fe/ml and 1.5 mg BSA/ml (higher iron concentration)
C. 1.25 mg Fe/ml and 5.0 mg BSA/ml (higher BSA concentration)
D. 3.75 mg Fe/ml and 5.0 mg BSA/ml (higher iron and BSA concentrations)

Immediately after precipitation but before any washing procedures, a sample was counted to quantitate the amount of radioactive label in the mixture. Then the particles were centrifuged, washed, resuspended, and counted. The results showed complete utilization of the BSA (incorporation into the magnetite pellet) for mixtures A and B, only 60% incorporation in the high-BSA sample (C), and a return to complete incorporation when the amount of iron was elevated to return to approximately the original ratio of iron to protein (sample D). Assuming that the iron was completely converted to magnetite ($Fe_3O_4$), the compositions of the four preparations were:

A. 46% protein, 54% magnetite
B. 22% protein, 78% magnetite
C. 63% protein, 37% magnetite
D. 49% protein, 51% magnetite The stability of the protein-magnetite particles against loss of BSA during sedimentation and resuspension with sonication was tested. After resuspension, particles were again "salted out" and radioactive BSA left behind in the supernatent was counted. An average of 40% (st. dev.=11%) of the counts which had been incorporated into the particles was lost. When the process was repeated, the losses in the next wash where less (14%, st. dev.=4%).

EXAMPLE 5

Demonstration of Magnetic Immunoassay Using Particles Coupled to an Antigen

Particles were precipitated and coupled to human IgM with SPDP, as described in Example 2 above, to make a magnetic antigen. The particle-IgM magnetic antigen bound commercial antibody against human IgM to which was coupled alkaline phosphatase enzyme (Ab-AP). A 1:500 dilustion of Ab-AP was incubated with approximately 250 micorgrams of IgM-magnetite in 100 micro-liters of phosphate containing 1% BSA. The amount of Ab-AP which bound to the IgM-magnetite was quantitated by passing the incubation mixture through a small magnetic filter. The filter bed was then washed with excess buffer, and loaded with buffer containing enzyme substrate. After 15 minutes incubation, the buffer was eluted and the amount of reaction product generated by enzyme captured on the filter bed was determined by measuring the optical density.

The above procedure formed the basis of a competitive immunoassay for human IgM. When small amounts of free IgM were added to the incubation mixture, the uptake of enzyme by the magnetite-antigen was specifically inhibited. The decrease in enzyme activity on the filter as a function of IgM in the incubation mixture was graphed to produce a calibration curve which allowed the process to be used as a competitive immunoassay to measure unknown amounts of IgM. The sensitivity was approximately 0.15 mg/ml (the concentration of IgM which resulted in 50% reduction in the specific capture of enzyme activity on the filter).

EXAMPLE 6

Direct Production of Particles Containing Antibodies which Retain Activity through Preparation Seven precipitation reactions were performed using mixtures of BSA and goat antibody (IgG fraction of goat anti-rabbit-immunoglobulins). The total amount of antibody in each was either 0.75 or 0.375 mg/ml. To this was added zero BSA, or enough BSA to bring the total protein up to 0.375, 0.75, 1.5 or 3.0 mg/ml. To each 2-ml sample was added 3.5 mg $FeCl_2$ and 7.0 mg $FeCl_3$. Particles were precipitated by the addition of 20 microliters of 30% $NH_4OH$, to bring the pH to 9.4. The preparations were then neutralized with acetic acid and spun down in a centrifuge and washed. The pelleted particles were resuspended with 2 minutes of sonication each. Half of each preparation was treated with the bifunctional reagent EGS (0.31 mg/ml) for several hours. After EGS treatment, particles were salted out with 1.5M NaCl, washed and resuspended with 1 minute sonication each.

The particles which were made with IgG (no BSA), and not EGS-treated, spontaneously settled out of suspension within about 24 hours. This was true of both the 0.75 mg/ml and the 0.375 mg/ml preparations. In both cases, however, the half of the prep which received the EGS treatment was stable in suspension and could be used.

Twelve samples were tested for goat-anti-rabbit-Ig activity by hemagglutination. A series of microtiter wells was set up containing sheep red blood cells (SRBC) and a sub-agglutinating concentration of rabbit antibody against SRBC. In each series, particles were added in concentrations which decreased two-fold in each successive well in the series. After several hours, the maximum well in which agglutination could be seen was read for each series. More active particles agglutinated at lower concentrations (larger well numbers). A table of results for the 12 preparations tested is given below.

TABLE I

Hemagglutination Results
Goat-anti-Rabbit Particles

| Total Protein in Precipitation | 0.375 mg/ml Ab in Precipitation | | 0.75 mg/ml Ab in Precipitation | |
|---|---|---|---|---|
| | No EGS | +EGS | No EGS | +EGS |
| 0.375 mg/ml | <S> | 3.5 | — | — |
| 0.75 mg/ml | 8.5 | 8.5 | <S> | 6.5 |
| 1.5 mg/ml | 8.5 | 8.0 | 9.5 | 10.5 |
| 3.0 mg/ml | 7.5 | 7.5 | 9.0 | 9.5 |

<S> = settled and so not tested in hemagglutination
Note: Fractional wells refer to pattern in which last well was not definitively agglutinated (Eg 9.5 = 9 wells agglutinated and tenth one partially so).

After two weeks storage at 4° C., hemagglutination was repeated from the samples which were made with 1.5 mg/ml total protein. Activity was essentially unchanged. Specificity of binding was demonstrated by the fact that no hemagglutination was seen in a control series of wells in which the anti-SRBC antibody was omitted.

Conclusions:
 (i) Antigen binding activity was hardly affected by EGS. In particles made with the same total protein, more activity was seen in preparations which contained greater amounts of Ab.
 (ii) In particles which contained either amount of Ab, but increasing amounts of BSA, improvements were seen up to 1.5 mg/ml total protein, and a slight drop-off in activity above that point.

EXAMPLE 7

Experiments were performed on magnetic particles containing $^{125}$I-labelled protein (HSA) in order to assess the stability of the particles with respect to protein composition.

Materials and Methods

Particles were prepared using $^{125}$I-labelled BSA that was iodinated by the ICl method. Three preparations were made containing total protein concentration of 0.05, 0.5 and 1.0 mg/ml of HSA. Each of these samples was prepared using the same amount of Fe. The relative proportions of "hot" and "cold" protein were adjusted such that the specific activity (4,000 c.p.m./ug) was the same in each case.

Results

In each case the amount of radio-label present in the supernatant immediately after particle formation was assessed. The amount of radio-label lost in the subsequent washing procedure was also determined. The final sonicated particle suspension was assayed for radio-label and Fe content and a protein/Fe ratio thus determined. The results are summarized in Table IV.

Under the conditions employed, final Fe content was approximately 1–1.56 mg/ml. Almost all of the labelled protein was incorporated into the initial precipitate in the case of preparations containing protein concentrations of 0.05 and 0.5 mg/ml. However, when protein was used at a concentration of 1 mg/ml a substantial proportion (approximately 30%) of the radio-label remained in the supernatant. This indicated that under these conditions, particle formation was efficient with regard to protein incorporation up to protein concentrations of 0.5 mg/ml. Higher protein concentration appeared to result in a saturation effect whereby excess protein remained in solution. This conclusion was further substantiated by the fact that the protein Fe ratio rose substantially in going from 0.05 to 0.5 mg/ml of protein, but no further increase was observed at 1.0 mg/ml.

The particles appeared to be relatively stable with regard to protein content throughout the washing procedure. (Significantly, the particles formed at high HSA concentration, lost more radio-label during the subsequent washing of the particles). It should also be noted that some of the loss of $^{125}$I-label may be accounted for by the loss of small but intact protein/magnetite particles.

Experiments were also performed in which the presence of free protein in these particle preparations was assessed by gel filtration. Preliminary experiments indicated that very little of the protein appeared to become "particle-free" after sonication. Also, no further protein appeared to "leach-off" when preparations were stored for up to 7 days. Furthermore, a second sonication did not appear to increase the proportion of free protein.

TABLE II

| Original Protein Concentration (mg/ml) | 0.05 | 0.5 | 1.0 |
|---|---|---|---|
| Original $^{125}$I-HSA (c.p.m.) | $1.10^6$ | $10.10^6$ | $20.10^6$ |
| 1st Supernatant (%) (5 mls) | 2.2 | 7.2 | 28 |
| Precipitated Particles* (%) | 98/100 | 93/100 | 72/100 |
| 1st Wash (%) (20 ml) | 3.5 | 3.5 | 2.7 |
| 2nd Wash (%) (20 mls) | 7.5 | 8.2 | 5.6 |
| 3rd Wash (%) (20 mls) | 4.5 | 8.3 | 21 |
| Sonicated Particle Suspension (%) | 83 | 78 | 70 |
| Fe Content (mg/ml) | 1.1 | 1.2 | 1.6 |
| Protein:Fe ratio | 1:30 | 1:3 | 1:3 |

*Obtained by difference

By the above technique, a polymer having reactive groups may be employed to provide a photo-activatable particle which may then be coupled to specific biofunctional compounds.

EXAMPLE 8

Comparative Example

In an attempt to replicate the preparative procedures of Molday and compare these to the procedures of the present invention, two series of reaction mixtures were prepared. The first series of mixtures began with the dextran and iron concentrations as taught by Molday and serially decreased dextran concentrations by powers of 10 in order to assess dextran concentration effects upon final particle characteristics. The second series of reaction mixtures began at dextran and iron concentrations in accordance with the present invention and serially increased dextran concentrations by powers of 10. The results of these series of preparations are summarized in Table III.

TABLE III

| Procedure | Fe(III) (mg/ml) | Fe(II) (mg/ml) | Dextran (mg/ml) | Results— | After Base Addition | After Heating (Molday Only) | After Sonication |
|---|---|---|---|---|---|---|---|
| Molday | 75 | 32 | 250 | | Stable Susp. Non-Magnetic | Stable Suspension Magnetic | NA |
| | Same | — | 25 | | Magnetic Ppt. | No change | Stable Magnetic Susp. |
| | Same | — | 2.5 | | Same | — | — |
| | Same | — | 0.25 | | Same | — | Non-Resuspendable |
| Example 1 | 4 | 1.6 | 0.25 | | Magnetic Ppt. | = | Stable Magnetic Susp. |
| | Same | — | 0.5 | | Amber Solut'n. | = | NA |
| | Same | — | 1.0 | | Same | = | NA |
| | Same | — | 256 | | Same | = | NA |
| Example 1 | 4 | 1.6 | 0.0025 | | Magnetic Ppt. | = | Stable Magnetic Susp. |
| | Same | — | 2.5 | | Amber Solut'n. | = | NA |

Notes:
NA = Not Attempted
= = Not Applicable to procedure used.

As is apparent from the comparative data, preparations in accordance with procedures taught by Molday fails to yield resuspendable particles. As concentrations of dextran are decreased toward the range employed in the present invention, the quality of product particle is degraded and the suspension of these particles becomes unstable. In contrast, concentrations of dextran and iron as taught by the present invention yield marginally acceptable stable suspensions of weakly magnetic particles. As dextran concentrations are increased toward that taught by Molday, however, a failure to precipitate results and no particles are produced. This divergence in conditions, as well as certain qualitative differences in particle size and iron to polymer ratio, are indicative of the extreme differences between the process and product taught by Molday and that of the present invention.

From the foregoing examples, the following conclusions have been drawn by the present inventors:
i) The particles of the present invention are
  a) Magnetic
  b) Stable in Aqueous Suspension
  c) Resuspendable
  d) Small (and thus filter sterilizable)
  e) Easily produced to include a specific biological activity
  f) Clear in Suspension
ii) Particles may be produced and subsequently bonded to specific biofunctional ligands using conventional bifunctional reagents.
iii) Specific biofunctional ligands may also serve as the polymer during coprecipitation without a significant loss of biological activity.
iv) Treatment of particles with bifunctional reagents may improve overall stability, both of the particles and of suspensions, without excessively impacting on particle size.
v) The particles, when coupled to specific biofunctional ligands, may be used in magnetic immunoassays for biological materials of interest.
vi) The particles decrease the NMR relaxation time of neighboring protons in solutions or tissues. This decrease is most pronounced for the $T_2$ (spin-spin) relaxation.

While this invention has been described with reference to specific examples, it will nonetheless be understood by those skilled in the art that other variations of process conditions and parameters may be employed without departing from the true spirit of the invention. It is intended that the claims which follow should be construed to encompass all such variations.

Statement of Industrial Utility

The present invention comprises novel magnetic-polymer particles and methods for making them. These particles are useful in a variety of biological/medical fields including cell capture, use as a contrast reagent for NMR imaging, immobilized enzyme reactors, immunoassay, and other analytical and diagnostic techniques.

We claim as our invention:

1. A method of separating a target substance from a non-target substance within a fluid mixture, comprising the steps of:

combining the fluid mixture with resuspendable, magnetic-polymer particles in a container, to produce a suspension comprising a magnetic component and a non-magnetic component, wherein the magnetic component comprises magnetic particles bound to the target substance through at least one substance on the surface of the magnetic particles which directly or indirectly binds to the target substance and the non-magnetic component comprises the remainder of the fluid mixture, including the non-target substance, and wherein the magnetic-polymer particles are produced by a process comprising the steps of:
   (a) combining a first aqueous solution of at least two species of transition metal ions capable of reacting with each other to form a magnetic precipitate and a polymer having available coordination sites in proportions adapted to produce a resuspendable product;
   (b) reacting said transition metal ions in the presence of said polymer to form a magnetic precipitate comprising magnetic-polymer particles; and
   (c) recovering said magnetic-polymer particles;
   generating in the container, a magnetic field;
   attracting the magnetic particles toward a collection surface; and
   collecting the magnetic component upon the collection surface, thereby separating the target substance from the non-target substance.

* * * * *